United States Patent [19]
Khatchatrian et al.

[11] Patent Number: 5,911,957
[45] Date of Patent: Jun. 15, 1999

[54] OZONE GENERATOR

[76] Inventors: Robert G. Khatchatrian; Ashot P. Khatchatrian; Asmik Aruntyunyan, all of 809 E. Chestnut St., #8, Glendale, Calif. 91205; Morev Sergey Nikolaevich, Geodezivsheskaja-Str., Nos 23, Flat 60, 630087, Novosibirsk, Russian Federation

[21] Appl. No.: 08/956,709

[22] Filed: Oct. 23, 1997

[51] Int. Cl.$^6$ .................................................. B01J 19/12
[52] U.S. Cl. ........................................ 422/186.07; 422/28
[58] Field of Search ................................ 422/186.07, 28

[56] References Cited

U.S. PATENT DOCUMENTS

| | | | |
|---|---|---|---|
| 5,364,600 | 11/1994 | Stiehl et al. | 422/186.07 |
| 5,437,843 | 8/1995 | Kuan | 422/186.07 |
| 5,503,809 | 4/1996 | Coate et al. | 422/186.18 |
| 5,630,990 | 5/1997 | Conrad et al. | 455/186.07 |
| 5,641,461 | 6/1997 | Ferone | 422/186.07 |
| 5,667,756 | 9/1997 | Ho | 422/186.18 |

*Primary Examiner*—Daniel J. Jenkins
*Attorney, Agent, or Firm*—Knobbe Martens Olson & Bear, LLP

[57] ABSTRACT

The present invention relates to an ozone generator comprised of a discharge means and a reflecting screen. The discharge means comprises a rough-surfaced dielectric element with central aperture and rectangular cross-section sandwiched between a first electrode and a second electrode. The first electrode is comprised of a plurality of helical windings that contact a plurality of flanges on the dielectric element and the second electrode is comprised of an electrically conductive coating which overlies the rough surface of the dielectric element. The first electrode is aligned with respect to the central aperture, dielectric element, and the second electrode such that a constant distance of separation between the electrodes is maintained along the entire length of the discharge means. The reflecting screen, joined to the discharge means by a plurality of mounting brackets, directs accumulated ozone away from the ozone generator and toward an intended site for treatment. The disclosed invention converts oxygen to ozone with great efficiency and, unexpectedly, the fusion of the second electrode with the surface of the dielectric element provides improved ozone recovery by rapidly dissipating heat generated by the discharge means.

31 Claims, 6 Drawing Sheets

OZONE GENERATOR

BACKGROUND OF THE INVENTION

Ozone is a powerful oxidizing agent that has many industrial and household uses. Ozone effectively kills bacteria, inhibits fungal growth, and inactivates many viruses, cysts, and spores. In addition, soaps, oils, and chloramines can be rendered environmentally safe by ozone treatment. The antiseptic properties of ozone are useful for water purification, room sanitation, equipment sterilization, and food preservation.

There are several known methods for producing ozone from air or other oxygen-containing gases. A number of these processes generate ozone by passing an oxygen-containing gas between two electrodes, separated by a dielectric material—the oxygen is converted to ozone as it travels through the electrical corona. Ozone has a half-life of only about 22 minutes at ambient temperatures, and at higher temperatures the rate of ozone decay is accelerated. An efficient ozone generator should, therefore, produce a high concentration of ozone without generating appreciable heat.

To this aim, several modifications on the basic corona discharge ozone generator have been developed. U.S. Pat. No. 5,409,673 relates to an ozone generator characterized by an outer electrode overlying a portion of a dielectric tube filled with a mass of helical windings which serves as an inner electrode. Similarly, U.S. Pat. No. 5,554,344 teaches the enhancement of ozone production by employing electrodes with a jagged surface while U.S. Pat. No. 4,981,656 teaches that an electrode of polygonal shape provides uniform gas discharge at low electrical voltages. Furthermore, with regard to heat dissipation, U.S. Pat. No. 4,770,858 teaches the benefits of coating the surface of a dielectric tube with non-conductive particles of inorganic material.

Despite the numerous beneficial applications for ozone and repeated attempts in the prior art to invent an efficient ozone generator, such a discovery has not yet occurred. The failure of the prior art to provide an efficient ozone generator can be attributed to three persistent problems: improperly aligned electrodes, accumulation of heat generated by the electrical discharge, and the lack of a means to direct freshly made ozone away from the apparatus to a site intended for treatment. The need for a simple and compact apparatus which efficiently produces and rapidly disperses ozone without accumulating an appreciable amount of heat is manifest.

SUMMARY OF THE INVENTION

The present invention discloses a new apparatus and method for producing ozone by electrical silent discharge. As disclosed herein, an ozone generator, is comprised of a silent discharge means joined to a reflecting shield. The discharge means comprises a rough-surfaced dielectric element of rectangular shape, a first electrode, and a second electrode. The dielectric element is sandwiched between the first electrode and the second electrode and both electrodes are connected to a high frequency (HF) converter.

The first electrode is comprised of a plurality of helical windings that contact a plurality of flanges on the dielectric element and the second electrode is comprised of an electrically conductive coating which overlies the rough surface of the dielectric element. The rectangular shape of the dielectric element facilitates the alignment of the electrodes, and the flanges maintain this aligned position. The fusion of the second electrode with the surface of the dielectric element significantly improves ozone recovery by rapidly dispersing heat as it is generated, and the reflecting screen directs accumulated ozone away from the ozone generator and toward an intended site for treatment.

DETAILED DESCRIPTION OF THE PREFERRED EMBODIMENTS

The present invention will be described more fully hereinafter with reference to the accompanying drawings, in which preferred embodiments of the invention are shown. This invention may be embodied in many different forms, however, and should not be construed as limited to the embodiments set forth within. Applicants provide these embodiments so that this disclosure will be thorough and complete, and willfully convey the scope of the invention to those skilled in the art.

Figure 1:
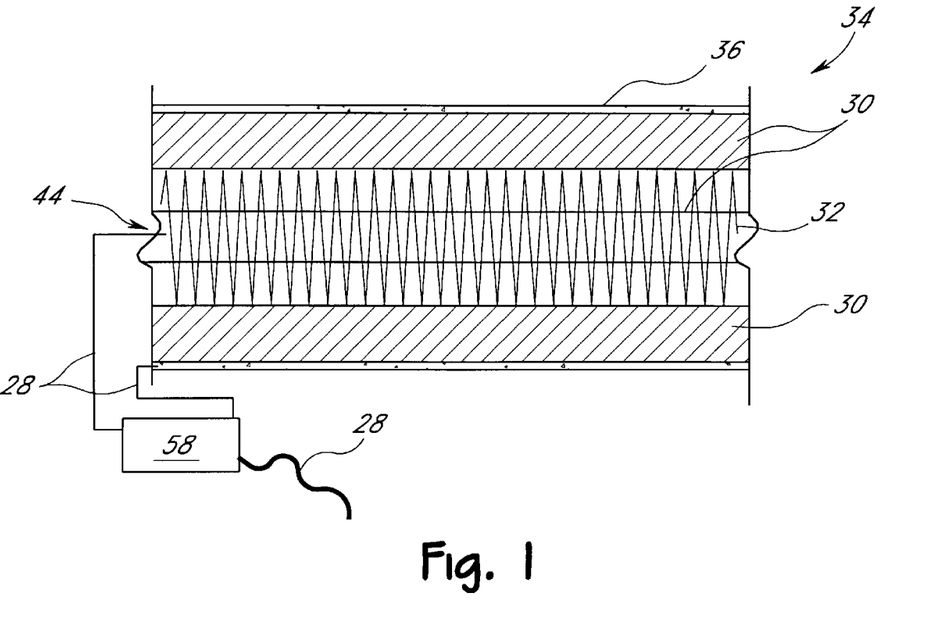
FIG. 1 is a sectional side view of a first embodiment of a silent discharge means attached to a HF converter, taken at arrow 1 of FIG. 2.
Figure 2:
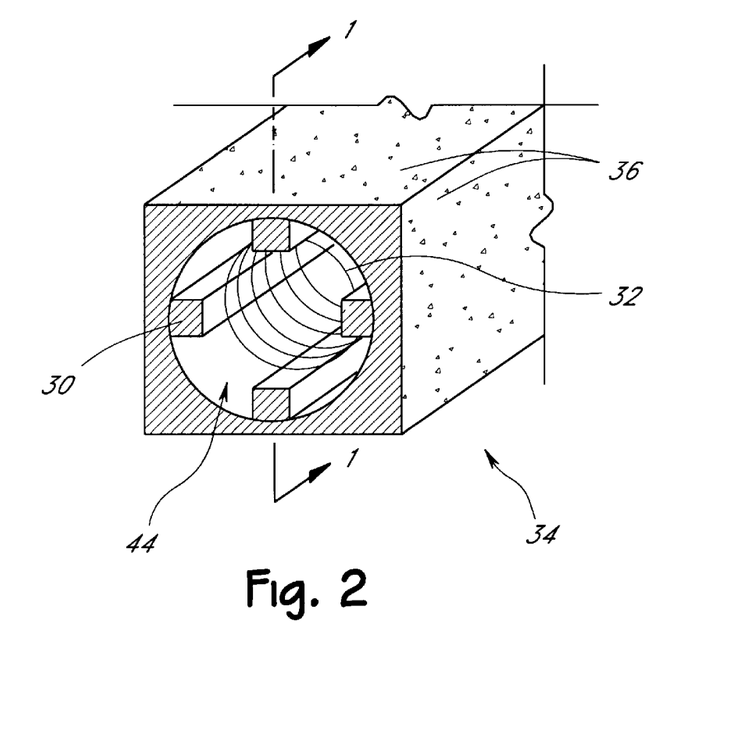
FIG. 2 is a cross-sectional view of the first embodiment of the silent discharge means.
Figure 3:
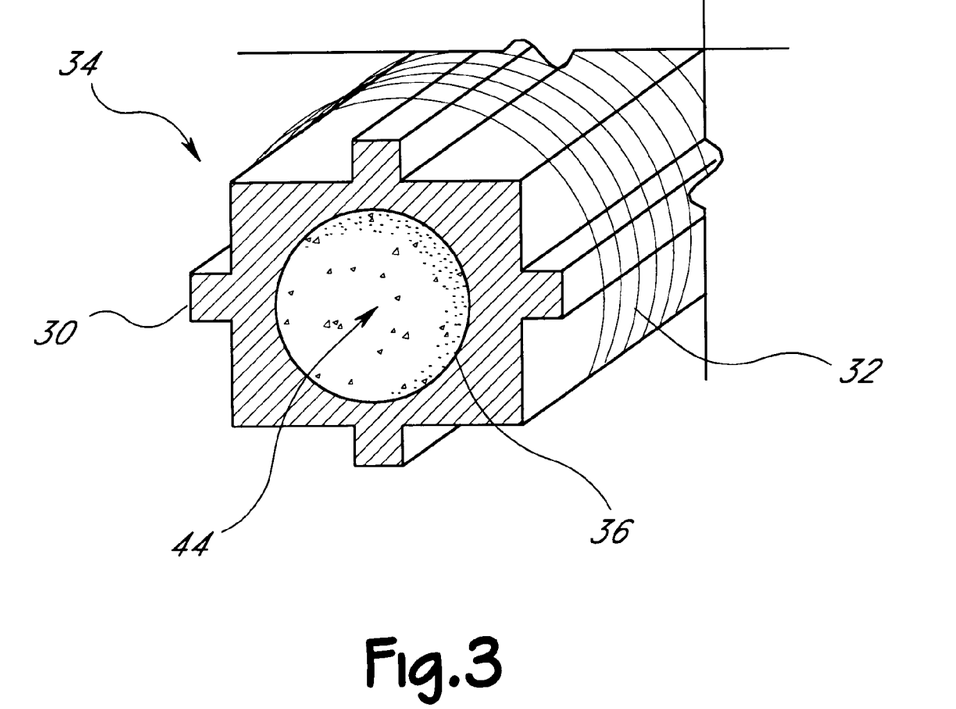
FIG. 3 is a cross-sectional view of a second embodiment of the discharge means.
Figure 4:
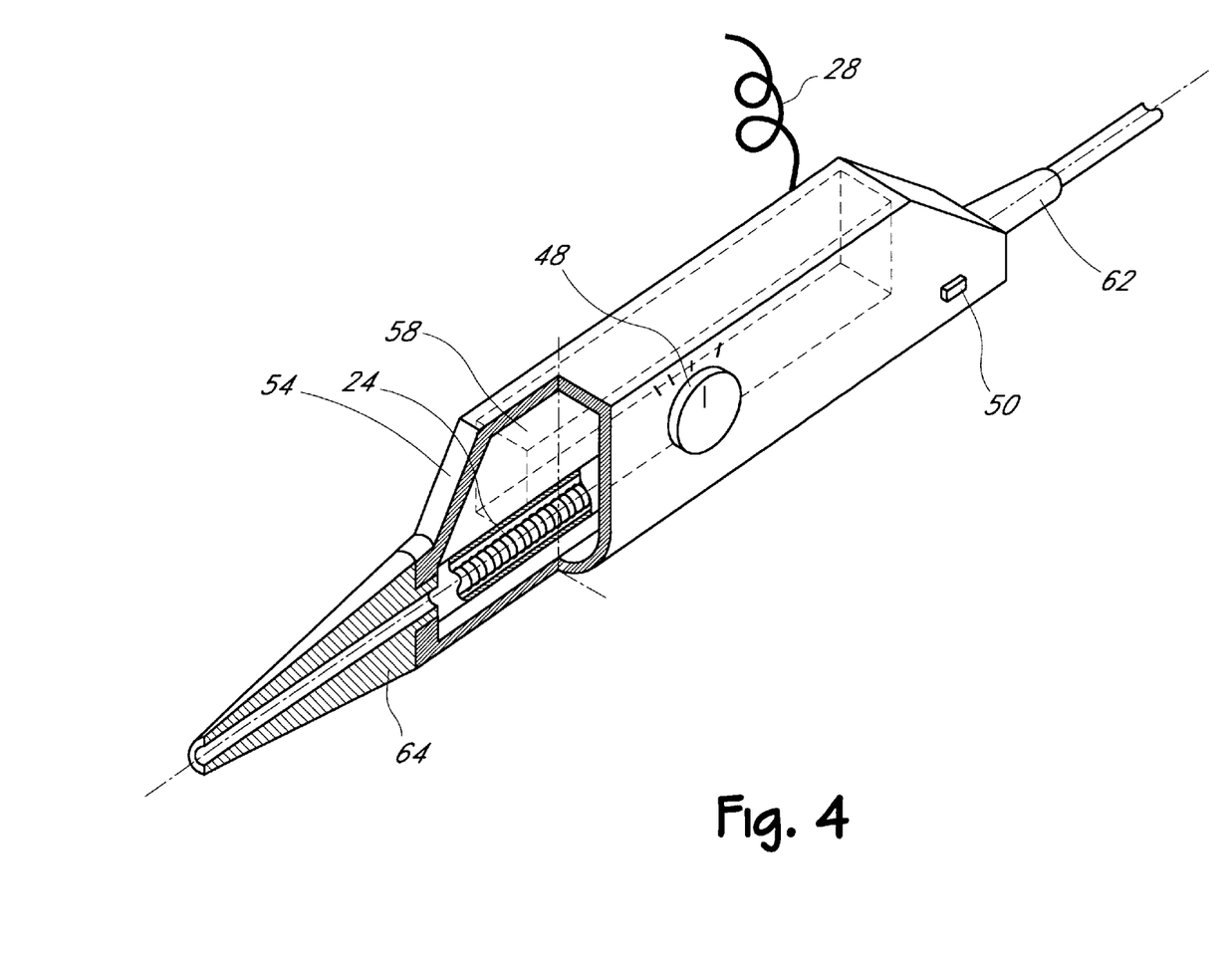
FIG. 4 is a perspective view of a first embodiment of an ozone generator according to the present invention (without reflecting screen).

As shown in FIGS. 1–8, an ozone generator is comprised of a discharge means 24 optionally connected to a reflecting screen 22. The discharge means 24 is connected to a high frequency converter (HF converter) 58 which is in turn connected to a power supply 20. The power supply 20 is either a storage battery (FIG. 6, 8) or normal line current from an electrical network (110 or 220 volts) (FIG. 4, 5, 7). Optional electrical leads 28 may be used to connect the high frequency converter 58 to the discharge means 24 and the power supply 20. FIGS. 1–3 reveal that the discharge means 24 is comprised of a rough-surfaced dielectric element 34 of rectangular shape, a central aperture 44, a first electrode 32, a second electrode 36, and a plurality of flanges 30. The electrode 32 and 36 are attached to the high frequency (HF) converter 58, which is in turn attached to the power supply 20. The power supply is either a battery or line current from an electrical network.

In a first embodiment of the discharge means 24, illustrated in FIGS. 1 and 2, the first electrode 32 is comprised of a plurality of helical windings that are mounted inside the central aperture 44 in an aligned position. Alignment of the first electrode 32 with respect to the central aperture 44, dielectric element 34, and the second electrode 36 is necessary to ensure uniform discharge at low voltages and to reduce the accumulation of heat at the dielectric element 34 and the electrodes 32 and 36. As used in this disclosure, the intended meaning of the word alignment and derivatives thereof encompasses the position of the first electrode 32 with respect to the central aperture 44, the dielectric element 34, and the placement of the first electrode 32 in a manner that maintains a constant distance of separation between the electrodes 32 and 36 along the entire length of the discharge means 24. The rectangular shape of the dielectric element 34 facilitates the determination of the position of the alignment of the first electrode 32, and flanges 30 hold the first electrode 32 in the properly aligned position. The helical windings of the first electrode 32 comprise a spiral shape. The first electrode is held in position inside the dielectric element 34 through the elastic nature or spring-like behavior of the spiral. The first electrode 32 is generally the same length as the dielectric element 34, although a first electrode 32 of any size can be constructed and mounted within a larger-sized dielectric element 34. The first electrode 32 of the first embodiment of the discharge means 24 may have 1 winding per cm to 100 windings per cm, or more desirably 2 windings per cm to 50 windings per cm, or preferably 2 windings per cm to 20 windings per cm. Similarly, the diameter of the filament used to construct the helical windings for this embodiment may include 0.001 mm to 1 mm, or more desirably 0.01 mm to 0.5 mm, or preferably 0.1 mm to 0.14 mm. The helical windings of the first electrode 32 can be made from tungsten, nickel-chromium alloy, molybdenum, or other suitable metals. aperture can have a diameter of 0.1 mm 20 mm, more preferably 1 mm to 10 mm, and most preferably from 2 mm to 6 mm.

The dielectric element 34 has a rough surface which serves as the foundation for the second electrode 36, once the dielectric element 34 is overlaid with the electrically conductive coating serving as the second electrode 36. The rough surface on the dielectric element 34 can be made by sanding, chemical treatment, or by embedding the surface with electrically non-conductive particles. Particles suitable for embedding the surface of the dielectric element are glass or ceramic, but many equivalent particles would be known by one of skill in the art. Furthermore, there are many ways to create a dielectric element 34 with a rough surface, and any person of skill in the art could develop alternative means to fulfill this purpose of the invention. Discharge at low voltages is improved by the rough surface of the second electrode 36, and the intimate association of the second electrode 36 with the dielectric element 34 enables the rapid dispersion of heat generated by the discharge means 24.

The construction of the first embodiment of the discharge means 24 can be used to guide one of skill in the art to make and use the second embodiment of the discharge means 24, illustrated in FIG. 3. In the second embodiment, the first electrode 32 spirals around the outside of the dielectric element 34, and the dielectric element 34 has a central aperture 44 with a rough interior surface. Furthermore, the electrically conductive coating of the second electrode 36 overlies the rough surface inside the central aperture 44. The first electrode 32 is aligned with respect to the central aperture 44 and the second electrode 36, and flanges secure the first electrode 32 to the dielectric element 34 in the aligned position. The first electrode 32 of the second embodiment of the discharge means 24 may have 1 winding per cm to 100 windings per cm, or more desirably 2 windings per cm to 50 windings per cm, or preferably 2 windings per cm to 20 windings per cm. Similarly, the filament used to construct the helical windings for this embodiment has a diameter of 0.001 mm The flanges 30 which hold the first electrode 32 in an aligned position may be part of a single-piece dielectric element 34 or, alternatively, may be comprised of a material different than the dielectric element 34 and attached to the dielectric element 34 by conventional methods. The dimensions of the flanges 30 and their spacing within the central aperture 44 may depend on the type of ozone generator and its intended application. The dielectric element 34 may contain from 4 to 20 flanges 30, or desirably 4 to 10 flanges 30, or preferably 4 to 6 flanges 30.

The second electrode 36 of the first embodiment of the discharge means 24 comprises an electrically conductive coating that overlies the rough outer surface of the dielectric element 34. Suitable electrically conductive coatings include copper, silver, and aluminum, although one of skill in the art would be able to develop and/or use many equivalent coatings to fulfill the intended purpose of this element of the present invention. The electrically conductive coating can be applied by being sprayed or chemically deposited to a thickness of 0.1 microns to 100 microns or more desirably from 0.5 microns to 50 microns or preferably from 2 to 10 microns. The second electrode 36 preferably spans the entire length of the dielectric element 34, or alternatively, may overlay only a portion of the dielectric element 34.

The dielectric element 34 can be made from ceramic, but it is within the skill of anyone in the art to manufacture a dielectric element from many other suitable materials such as glass or PYREX. Alternatively, the surface of the dielectric element 34 facing the first electrode 32 can be a composite structure constructed of materials having different dielectric permeability and porosity such as ceramic and glass fiber. The thickness of the dielectric element 34 and the dimensions of the central aperture 44 may vary according to the apparatus and intended application, but, in general, the electrodes 32 and 36 are separated by a dielectric element 34 having a thickness of 0.01 mm to 10 mm or, more desirably, 0.05 mm to 2 mm or preferably 0.1 mm to 0.7 mm, and the central to 1 mm or more desirably 0.01 mm to 0.5 mm, or preferably 0.1 mm to 0.14 mm. The helical windings of the first electrode 32 may be made from tungsten, nickel-chromium alloy, molybdenum, or other suitable metals.

Figure 5:
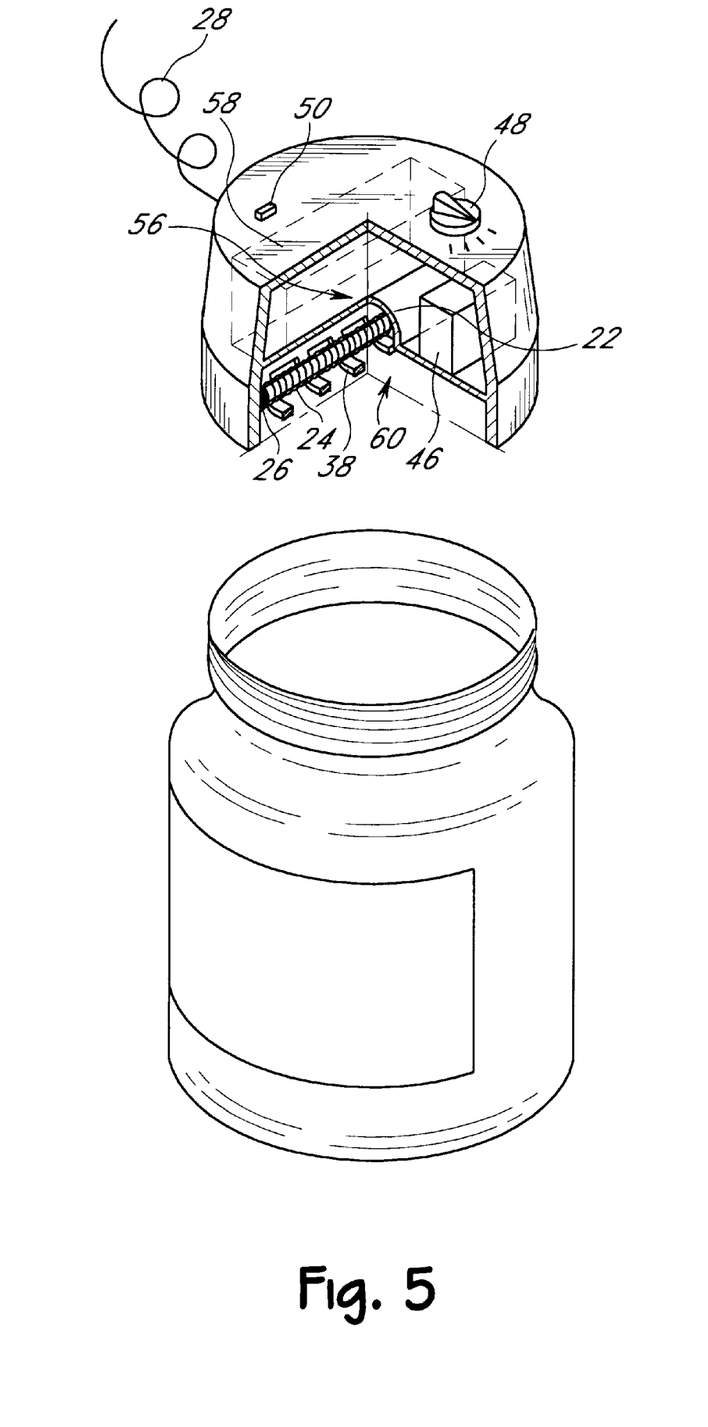
FIG. 5 is a sectional view of a second embodiment of the ozone generator according to the present invention.

The fabrication of reflecting screens 22 to accompany the embodiments illustrated in FIGS. 5–8 can be accomplished through routine experimentation by one of skill in the art given the disclosure that follows. Reflecting screens 22 are generally made from plastic or metal, but they can also be constructed from many other materials known to those of skill in the art. In FIG. 5, the reflecting screen 22 is a parabolic shape, and the dielectric element 34 of the discharge means 24 is joined to the reflecting screen 22 by a plurality of mounting brackets 26. Mounting brackets 26 can include many types of connectors whose compositions are frequently made of plastic but can be comprised of any other insulating material. By placing the discharge means 24 within the focus of the parabola of the reflecting screen 22, the flow of ozone can be directed to a site intended for sterilization.

FIG. 4 shows a first embodiment of the ozone generator in which the discharge means 24 is enclosed within a discharge housing 54. A switch 48 is connected to a high frequency converter 58 that joins to the power supply 20 and the discharge means 24. In the embodiment shown in FIG. 4, the power supply 20 is line current from an electrical network. A light emitting diode 50 is also connected to the high frequency converter 58 and indicates the operation of the ozone generator. A source of oxygen can be attached to an inlet 62 SO that ozone can be generated as the oxygen passes through the discharge means 24. Alternatively, the inlet 62 can be attached directly to the dielectric element 34 when using an embodiment of the invention with a hollow dielectric element, such as one with an internal electrode 32. The ozone exits the ozone generator through a sterilizing tip 64 which is constructed so that a variety of objects can be attached and sterilized. Objects which can be attached to the sterilizing tip of this embodiment include catheters, tubing, needles, bottles, and syringes. The sterilization of many other items can be achieved by this embodiment and the sterilization tip 64 can be modified by one of skill in the art to accommodate a multitude of medical devices.

Alternatively, as shown in FIG. 5 (embodiment 2), mounting brackets 26 and a protective shield 38 secure the discharge means 24 to a reflecting screen 22 shaped like a lid to a container. By placing this embodiment of the ozone generator over a matching container, items placed inside the container can be sterilized. According to this aspect of the present invention, an upper compartment 56 of the ozone generator houses a switch 48 joined to the timer 46, a light emitting diode 50, and a high frequency converter 58 (shown in phantom lines) joining the power source 20 and the discharge means 24. In this case, the power source is line current from an electrical network. The discharge means 24 is mounted in a lower compartment 60 of the ozone generator, and the reflecting screen 22 forms a barrier between the two compartments. By opening the switch 48, the timer 46 is set, and current from the power supply 20 is transferred through the high frequency converter 58 to the electrodes 32 and 36 and the light emitting diode 50. The light emitting diode indicates that the ozone generator is in operation. When the set time expires, the current to the high frequency converter 58, the electrodes 32 and 36, and the light emitting diode 50 is removed.

Figure 6:
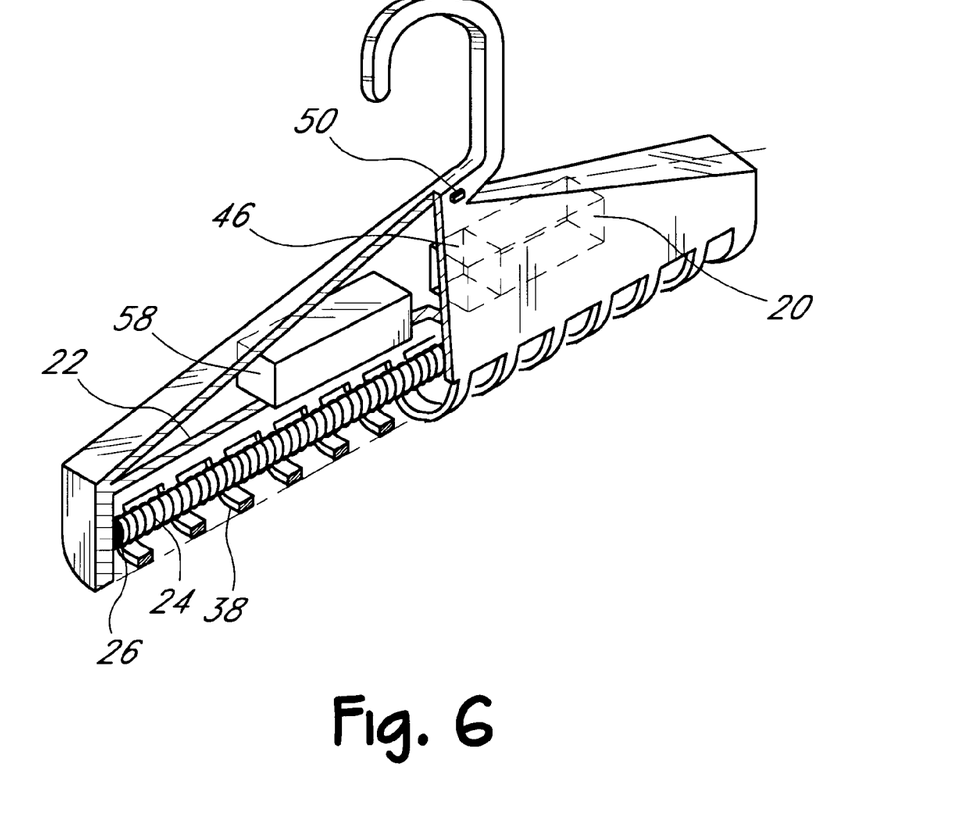
FIG. 6 is a sectional view of a third embodiment of the ozone generator according to the present invention.

The ozone generator illustrated in FIG. 6 is constructed similarly to the embodiment shown in FIG. 5 but takes the shape of a clothes hanger and provides a means to sterilize articles of clothing. As described above, the power supply 20 (shown in phantom lines), switch 48 (not shown), timer 46 (shown in phantom lines), high frequency converter 58, and light emitting diode 50 are isolated from the discharge means 24 by a barrier created by the reflecting screen 22. In this case, the power supply 20 is a battery.

Figure 7:
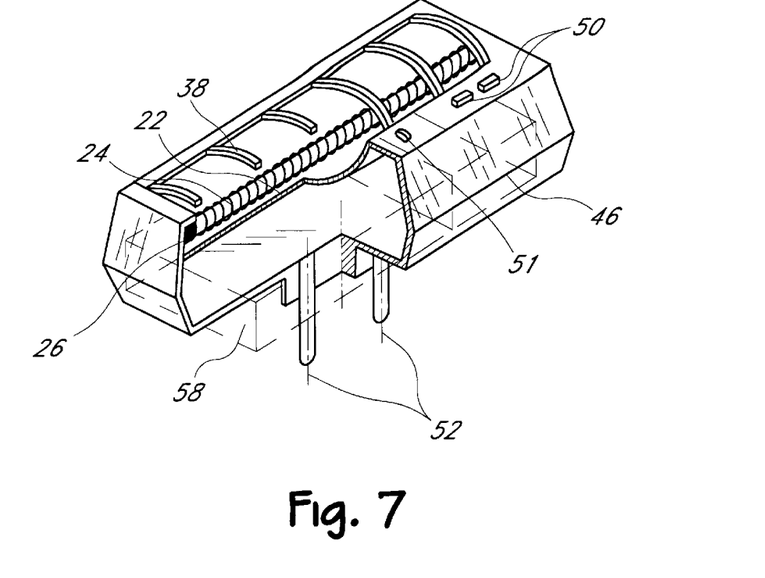
FIG. 7 is a sectional view of a fourth embodiment of the ozone generator according to the present invention.

Although the embodiment set forth in FIG. 7 is fabricated in much the same manner as the ozone generators described above, an adapter 52 attached to the high frequency converter 58 enables a user to draw current directly from an electrical outlet. A photo-cell 51 allows for automatic on/off switching depending on the light level. For example, the ozone generator can be set to operate automatically at night. The ozone generator pictured in FIG. 7 provides an efficient and economical means to deodorize or sanitize a room.

Figure 8:
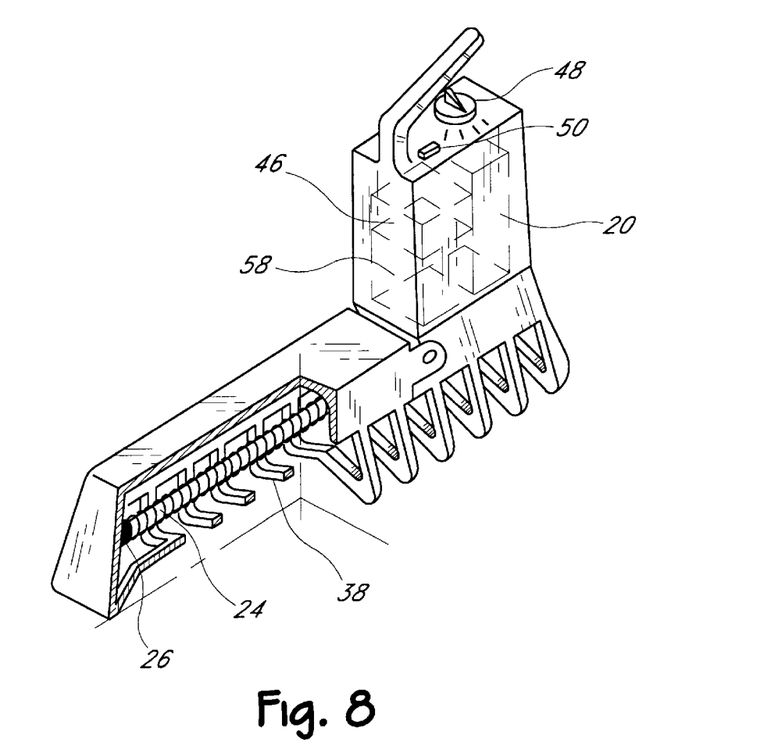
FIG. 8 is a sectional view of a fifth embodiment of the ozone generator according to the present invention.

The apparatus shown in FIG. 8 can be used to deodorize shoes. This ozone generator is constructed in the same manner as the embodiments shown in FIGS. 5–7, but it is shaped so that the apparatus can be placed in a shoe.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that modifications and embodiments are intended to be included within the scope of the appended claims.

What is claimed is:

1. An apparatus for generating ozone from an electrical discharge in an oxygen containing gas, the apparatus comprising:

a dielectric element of rectangular cross-section having a rough surface;

a plurality of flanges joined to the dielectric element;

a first electrode comprised of a plurality of electrically conductive helical windings in contact with the flanges; and a second electrode comprised of an electrically conductive coating which overlies the rough surface of the dielectric element;

wherein said flanges provide continuous spacing between the first electrode and the dielectric.

2. The apparatus according to claim 1, further comprising a reflecting screen joined to the dielectric element to direct flow of ozone.

3. The apparatus according to claim 1, wherein the dielectric is a composite structure comprising at least two materials of different dielectric permeability.

4. The apparatus according to claim 1, wherein the roughness of the dielectric is achieved by machining the dielectric surface.

5. The apparatus according to claim 1, wherein the roughness of the dielectric is achieved by chemically treating the dielectric surface.

6. The apparatus according to claim 1, wherein the roughness of the dielectric is achieved by embedding the dielectric surface with particles that are not electrically conductive.

7. The apparatus according to claim 1, wherein the second electrode comprises an electrically conductive material of non-solid structure.

8. The apparatus according to claim 7, wherein the electrically conductive material of non-solid structure comprises a gel.

9. The apparatus according to claim 7, wherein the electrically conductive material of non-solid structure comprises a colloid.

10. The apparatus according to claim 1, wherein the dielectric element comprises an aperture.

11. The apparatus according to claim 10, wherein the flanges are inside the aperture and the first electrode is in contact with the flanges.

12. The apparatus according to claim 10, wherein the flanges are outside the aperture and the first electrode is in contact with the flanges.

13. The apparatus according to claim 10, wherein the flanges of the dielectric are inside the aperture and the electrically conductive coating of the second electrode is overlaid onto the surface of the dielectric outside the aperture.

14. The apparatus according to claim 10, wherein the flanges of the dielectric are outside the aperture and the electrically conductive coating of the second electrode is overlaid onto the surface of the dielectric inside the aperture.

15. The apparatus according to claim 10, wherein the first electrode is aligned with respect to the aperture and the second electrode and flanges maintain the aligned position.

16. A method for generating ozone from an electrical discharge in an oxygen containing gas comprising the steps of:

providing a dielectric element of rectangular cross-section having a surface with a plurality of flanges joined with the dielectric and a surface opposite the surface with a plurality of flanges, a first electrode comprised of a plurality of electrically conductive helical windings facing the plurality of flanges, and a second electrode comprised of an electrically conductive coating on the surface of the dielectric element opposite to the surface with the plurality of flanges;

energizing the first and second electrodes with electrical power to generate the electrical discharge; and passing the oxygen containing gas through the electrical discharge so as to generate ozone;

wherein said flanges provide continuous spacing between the first electrode and the dielectric.

17. The method according to claim 16, further comprising directing flow of the ozone through a reflecting screen of parabolic shape.

18. The method according to claim 16, wherein the dielectric is a composite structure comprising at least two materials of different dielectric permeability.

19. The method of claim 16, wherein the second electrode comprises a layer of electrically conductive material.

20. The method according to claim 16, further comprising flanges which contact the first electrode.

21. The method according to claim 20, wherein the flanges maintain the first electrode in an aligned position.

22. A method for sterilizing the contents of a container comprising the steps of:

providing an ozone generator having the shape of a lid to a container comprised of a dielectric element of rectangular cross-section having a surface with a plurality of flanges and a surface opposite the surface with a plurality of flanges, a first electrode comprised of a plurality of electrically conductive helical windings facing the surface with a plurality of flanges, a second electrode comprised of an electrically conductive coating on the surface of the dielectric element opposite the surface with a plurality of flanges, and a reflecting screen attached to the dielectric element;

depositing materials intended for sterilization in the container;

joining the ozone generator to the container;

energizing the first and second electrodes with electrical power to generate an electrical discharge; and passing an oxygen containing gas through the electrical discharge so as to generate ozone;

wherein said flanges provide continuous spacing between the first electrode and the dielectric.

23. The method according to claim 22, wherein the ozone generator further comprises a timer, a switch joined to the timer, and a high frequency converter joined to the electrodes.

24. A method for treating clothing with ozone comprising the steps of:

providing an ozone generator having the shape of a clothes hanger comprised of a dielectric element of rectangular cross-section having a surface with a plurality of flanges and a surface opposite the surface with a plurality of flanges, a first electrode comprised of a plurality of electrically conductive helical windings facing the surface with a plurality of flanges, a second electrode comprised of an electrically conductive coating on the surface of the dielectric element opposite to the surface with a plurality of flanges, and a reflecting screen of parabolic shape attached to the dielectric element;

attaching materials intended for sterilization to the ozone generator;

energizing the first and second electrodes with electrical power to generate an electrical discharge; and passing an oxygen containing gas through the electrical discharge so as to generate ozone;

wherein said flanges provide continuous spacing between the first electrode and the dielectric.

25. The method according to claim 24, wherein the ozone generator further comprises a portable power supply, a timer joined to the portable power supply, a switch joined to the timer, and a high frequency converter joined to the power supply and the electrodes.

26. A method for sanitizing shoes comprising the steps of:

providing an ozone generator of oblong shape comprised of a dielectric element of rectangular cross-section having a surface with a plurality of flanges and a surface opposite the surface with a plurality of flanges, a first electrode comprised of a plurality of electrically conductive helical windings facing the surface with the plurality of flanges, a second electrode comprised of an electrically conductive coating on the surface of the dielectric element opposite to the surface with a plurality of flanges, and a reflecting screen of parabolic shape attached to the dielectric element;

placing the ozone generator in a shoe;

energizing the first and second electrodes with electrical power to generate an electrical discharge; and passing an oxygen containing gas through the electrical discharge so as to generate ozone;

wherein said flanges provide continuous spacing between the first electrode and the dielectric.

27. The method according to claim 26, wherein the ozone generator further comprises a portable power supply, a timer joined to the portable power supply, a switch joined to the timer, and a high frequency converter joined to the power supply and the electrodes.

28. A method for deodorizing a room comprising the steps of:

providing an ozone generator comprised of a dielectric element of rectangular cross-section having a surface with a plurality of flanges and a surface opposite the surface with a plurality of flanges, a first electrode comprised of a plurality of electrically conductive helical windings facing the surface of the dielectric element with a plurality of flanges, a second electrode comprised of an electrically conductive coating on the surface of the dielectric element opposite to the surface with a plurality of flanges, and a reflecting screen of parabolic shape attached to the dielectric element;

energizing the first and second electrodes with electrical power to generate an electrical discharge; and passing an oxygen containing gas through the electrical discharge so as to generate ozone;

wherein said flanges provide continuous spacing between the first electrode and the dielectric.

29. The method according to claim 28, wherein the ozone generator further comprises a timer, a switch joined to the timer, and a high frequency converter joined to the power supply and the electrodes.

30. The method according to claim 28, wherein the ozone generator further comprises an adapter for an electrical outlet.

31. A method for sterilizing a medical device comprising the steps of:

providing an ozone generator comprised of a dielectric element of rectangular cross-section having a surface with a plurality of flanges and a surface opposite the surface with a plurality of flanges, a first electrode comprised of a plurality of electrically conductive helical windings facing the flanges, a second electrode comprised of an electrically conductive coating on the surface of the dielectric element opposite the surface with a plurality of flanges, a tubular shaped reflecting screen that connects at one end to an inlet that can be joined to a source of an oxygen containing gas, and a sterilizing tip joined to the reflecting screen at the end opposite that in which the inlet is connected;

joining a source of an oxygen containing gas to the inlet;

energizing the first and second electrodes with electrical power to generate an electrical discharge; and passing an oxygen containing gas through the electrical discharge so as to generate ozone;

wherein said flanges provide continuous spacing between the first electrode and the dielectric.

* * * * *

UNITED STATES PATENT AND TRADEMARK OFFICE
CERTIFICATE OF CORRECTION

PATENT NO. : 5,911,957
DATED : June 15, 1999
INVENTOR(S) : Robert G. Khatchatrian, et al.

It is certified that error appears in the above-identified patent and that said Letters Patent is hereby corrected as shown below:

On the title page, item [76]:
Please change the name of the Third Inventor from
"Asmik Aruntyunyan" to --Asmik Aroutiounian--.

Signed and Sealed this

Twenty-first Day of December, 1999

Attest:

Q. TODD DICKINSON

*Attesting Officer*   *Acting Commissioner of Patents and Trademarks*